United States Patent
Jachowicz et al.

(10) Patent No.: US 6,207,778 B1
(45) Date of Patent: Mar. 27, 2001

(54) CONDITIONING/STYLING TERPOLYMERS

(75) Inventors: Janusz Jachowicz, Bethel, CT (US); Kou-Chang Liu, Wayne, NJ (US); Roger L. Mc Mullen, Jr., Bloomfield, NJ (US); Thomas Winkler, Maywood, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/307,211

(22) Filed: May 7, 1999

(51) Int. Cl.⁷ .......................... C08J 226/06; A61K 31/79
(52) U.S. Cl. .................. 526/258; 526/264; 526/328.5; 526/317.1; 526/318.4; 526/307.2; 526/307.6; 525/72; 525/283; 525/244; 428/78.24
(58) Field of Search .................... 526/258, 264, 526/195, 328.5, 317.1, 318.4, 307, 307.2, 307.6; 424/78.24, 70.12; 525/72, 283, 244, 93, 95.51

(56) References Cited

U.S. PATENT DOCUMENTS

| | | | | |
|---|---|---|---|---|
| 4,956,430 | * | 9/1990 | Tazi ........................................ | 526/195 |
| 5,321,110 | * | 6/1994 | Shih ....................................... | 526/264 |
| 5,603,919 | * | 2/1997 | Liu ......................................... | 424/47 |
| 5,609,865 | * | 3/1997 | Liu et al. ............................. | 424/78.24 |
| 5,626,836 | * | 5/1997 | Liu et al. ............................. | 424/47 |
| 5,830,438 | * | 11/1998 | Dupius .................................. | 424/45 |
| 5,997,853 | * | 12/1999 | Bolich, Jr. et al. ................ | 424/70.12 |
| 5,997,855 | * | 12/1999 | Liu ....................................... | 424/78.24 |
| 5,997,886 | * | 12/1999 | Peffly et al. ........................ | 424/401 |

* cited by examiner

Primary Examiner—David W. Wu
Assistant Examiner—Tanya Zalukaeva
(74) Attorney, Agent, or Firm—Walter Katz; William J. Davis; Marilyn J. Maue

(57) ABSTRACT

What is described herein are conditioning/styling terpolymers of vinylpyrrolidone (VP), dimethylaminopropyl methacrylamide (DMAPMA) and $C_9$–$C_{24}$ alkyl dimethylaminopropyl methacrylic acid quaternized monomers (QDMAPMA), in a defined compositional range. Hair and skin care compositions which include these terpolymers exhibit advantageous low tackiness and high humidity resistance.

12 Claims, No Drawings

CONDITIONING/STYLING TERPOLYMERS

BACKGROUND OF THE INVENTION

1. Field of the Invention

This invention relates to polymers for use in hair and skin care compositions, and, more particularly, to conditioning and styling terpolymers having advantageous low tackiness and high humidity resistance.

2. Description of the Prior Art

Copolymers of VP and DMAPMA have been used extensively as active components of hair and skin compositions. While these copolymers are generally suitable polymers for such products as conditioners and shampoos, it is desired to provide new polymers having improved performance characteristics in these and other personal care products.

SUMMARY OF THE INVENTION

What is described herein is a terpolymer of vinylpyrrolidone (VP), dimethylaminopropyl methacrylamide (DMAPMA) and $C_9$–$C_{24}$ alkyl dimethylaminopropyl methacrylic acid quaternized monomers (QDMAPMA), within a defined compositional range, for use in hair and skin care compositions, which are characterized by low tackiness and high humidity resistance.

DETAILED DESCRIPTION OF THE INVENTION

The terpolymers of the invention comprises the following X, Y, and Z monomers, having the formulas given below:

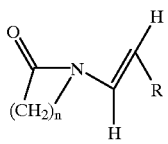
(X)

where:

X is a vinyl cyclic amide, e.g. vinyl pyrrolidone; n=3 to 6; R is H or $C_1$–$C_5$ alkyl and wt % of X=40–95; preferably 60–90;

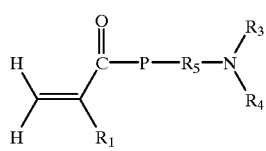
(Y)

where:

Y is a derivative of acrylic acid; P is O or $NR_2$; $R_1$, $R_2$, $R_3$, $R_4$ are independently H or $C_1$–$C_5$ alkyl; $R_5$ is $C_2$–$C_{16}$ alkyl alkylene; and wt % of Y=0.1 to 55; preferably 5–30;

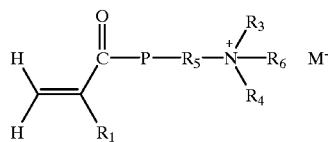
(Z)

where:

Z is a quaternized derivative of an acrylic acid; P is O or $NR_2$; $R_1$, $R_2$, $R_3$, $R_4$ are independently H or $C_1$–$C_5$ alkyl; $R_5$ is a $C_2$–$C_{16}$ alkylene; and $R_6$ is $C_9$–$C_{24}$ alkyl; M is a halide, tosylate or phosphate anion; and wt % of Z=0.25 to 50, preferably 1–30.

The terpolymers of the intention are hydrophobically-modified cationic polymers hating long alkyl-chains therein. A typical terpolymer thus has the following formulas:

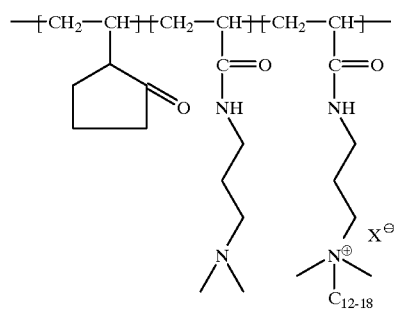

Ter (VP-DMAPMA-QDMAPMA)

Suitably, monomer Z is prepared by tosylating DMAPMA as follows:

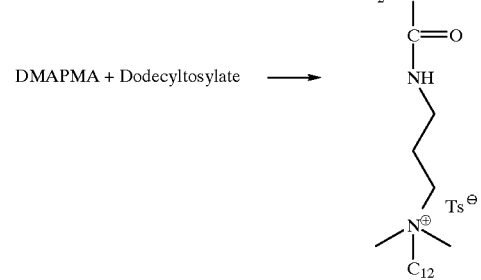

In preferred embodiments of the invention,

X is vinyl pyrrolidone;

Y is dimethylaminopropyl methacrylamide, and

Z is a $C_{12}$–$C_{18}$ alkyl quaternized derivative of an acrylic acid;

X is about 60–90 wt %, Y is about 5–30 wt % and Z is about 1–30 wt %; Z is $C_{12}$ alkyl quaternized monomer; the weight average molecular weight of the terpolymer is 200,000 to 2,000,000; preferably 400,000 to 800,000; it is water soluble or water dispersible; and forms a clear humidity resistant, hydrophobic film when cast upon a support surface; which is surface active and hydrolytically stable; and is a homogeneous terpolymer.

Cosmetic compositions of advantageous properties including about 0.1 to 10% by weight of the terpolymer can be prepared conveniently in this invention.

Preferably, the homogeneous terpolymers of the invention are made according to the method described by Kou-Chang Liu et al. in U.S. Pat. No. 5,626,836.

EXAMPLE 1

The preparation of (dodecyldimethyl methacryloimidopropyl ammonium tosylate). [DMAPMA-$C_{16}$Ts] A mixture of 360 g of dodecyl tosylate and 200 g of DMAPMA were slowly heated up to 70° C. without a solvent. Stirring was continued at 70° C. for 2 hours. Then the reaction was cooled to room temperature and solidified product was further used in polymerization without purification.

EXAMPLE 2

Terpolymer of VP/DMAPMA/DMAPMAA-$C_{12}$Ts Quat

N-Vinylpyrrolidone (VP) (280 g) and deionized water (1400 g) are charged into a 2-liter resin pot equipped with a gas inlet, liquid inlet, a thermometer, and a condenser. The pH of the solution is adjusted to about 7.5 with KOH. Then a stream of nitrogen is introduced which bubbles through the solution during the reaction. The solution in gradually heated to 65° C. for Lupersol® 11 catalyzed reaction, or to 78° C. for a Vazo® 67 initiated process. Then, DMAPMA (17.5 g) and DMAPMAA-$C_{12}$Ts quat (52.5 g) are added continuously and uniformly into the pot with vigorous stirring for 4 hours so that the relative concentrations of the monomeric VP, DMAPMA, and DMAPMAA-$C_{12}$Ts quat monomer remain practically constant throughout the reaction at predetermined levels.

As soon as DMAPMA and the DMAPMAA-$C_{12}$Ts quat are introduced into the pot, Lupersol® 11 (t-butylperoxy pivalate in mineral spirits) or Vazo® 67 2,2-azobis (2-methylbutanenitrile), catalyst is added. The rate of the addition of the catalyst is such that 2 ml of Lupersol is completely delivered in 4 hours. Then the solution is held for an additional 3 hours at 68° C. (or 78° C. for Vazo 67 initiator). The product is an aqueous solution of a homogeneous terpolymer of VP, DMAPMA and a DMAPMAA-$C_{12}$Ts quat has a predetermined composition indicative of the relative amounts of each monomer used in the process and is substantially free of any residual homopolymer or copolymer. The yield of the terpolymer product is substantially quantitative.

EXAMPLES 1–6

Terpolymers of VP/DMAPMA/QDMAPMAA-DTs (Dodecyl Tosylate Hydrophobe)

| Ex. | Composition (wt %) VP/DMAPMA/ QDMAPMAA-DTs | Conc % w/w | $M_w \times 10^3$ | D | $\eta \times 10^3$ [cps] | Resid VP [ppm] | Resid DMAPMA [ppm] | Resid HDMAPMA % $C_{12}$OH |
|---|---|---|---|---|---|---|---|---|
| 1 | 74/19.3/6.7 | 10 | 540 | 4.7 | 117 | 210 | <100 | 0.34 |
| 2 | 74/19.3/6.7 | 15 | 560 | 4.6 | 163 | 640 | <100 | 0.58 |
| 3 | 74/19.3/6.7 | 10 | 550 | 4.6 | 34.6 | 640 | <100 | 0.58 |
| 4* | 80/71/12.9 | 20 | — | — | 41.4 | — | — | — |
| 5* | 80/10.36/9.64 | 20 | — | — | 35 | — | — | — |
| 6* | 77/20/3 | 20 | — | — | 26.8 | — | — | — |

*Vazo 67 initiator used

EXAMPLE 7

Preparation of cocoyldimethyl methacrylamidopropyl ammonium tosylate

A mixture of 284.4 g of $C_{16}$–$C_{18}$ tosylate and 126.7 g of DMAPMA were slowly heated up to 70° C. without a solvent. Stirring was continued at 70° C. for 3 hours. Then the temperature was raised to 80° C. and maintained for 6 hours while stirring. Then the reaction was cooled to room temperature and solidified product was further used in polymerization without purification.

EXAMPLE 8

Terpolymer of VP/DMAPMA/DMAPMAA $C_{16}$–$C_{18}$Ts Quat

The copolymerization of VP/DMAPMA/DMAPMAA-$C_{16}$Ts Quat followed the same procedure as given in Example 2.

EXAMPLES 8–10

Polymers of VP/DMAPMA/DMAPMAA-$C_{16}$Ts (Hexadecyl Tosylate Hydrophobe)

| Ex. | Composition (wt %) VP/DMAPMA/ DMAPMAA-$C_{16}$Ts | Conc. % w/w |
|---|---|---|
| 8 | 74/19.3/6.7 | 15 |
| 9 | 74/20/6 | 20 |
| 10 | 77/20/3 | 20 |

EXAMPLE 11

Preparation of Lauryl-Dimethyl Methacrylamidopropyl Ammonium Chloride

A mixture of 350 g of DMAPMA and 280 g of chlorododecene (1.5:1) was stirred with 111.2 g of water (15%) and 6 drops of concentrated sulfuric acid. The reaction mixture was heated up to 95°0 C. and $N_2$ was bubbled through it. The conversion was followed by GC. After 24 hours the reaction mixture was cooled off (95% conversion of vinyl chloride) and product was further used in polymerization without purification.

EXAMPLES 12–17

Terpolymer of VP/DMAPMA/QDMAPMA Lauryl Chloride

The terpolymerization of VP/DMAPMA/DMAPMAA-$C_{16}$ Cl quat followed the same procedures as described in Example 2.

Terpolymer of VP/DMAPMA/QDMAPMA Lauryl Chloride
The terpolymerization of VP/DMAPMA/DMAPMAA-$C_{16}$ Cl quat followed the same procedure as described in Example 2.

| Ex. | Composition (wt %) VP/DMAPMA/ QDMAPMAA-LCL | Conc % w/w | $M_w$ $10^3$ | D | $\eta$ $\times 10^3$ [cps] | Resid VP [ppm] | Resid LCLA [ppm] |
|---|---|---|---|---|---|---|---|
| 12 | 77/70/3 | 20 | 615 | 5.5 | 28 | 600 | 400 |
| 13 | 74/70/6 | 20 | 510 | 5.4 | 35 | 600 | 800 |
| 14 | 71/70/9 | 20 | 485 | 6.2 | 64 | 500 | 1300 |
| 15 | 93.3/3.7/3 | 20 | 493 | 5.3 | 13 | 200 | 400 |
| 16 | 66.5/7.5/6 | 20 | 550 | 6.8 | 14 | 400 | 800 |
| 17 | 79.8/11.2/9 | 20 | 575 | 7.2 | 30 | 300 | 1300 |

EXAMPLE 18

Conditioning Cream Rinse Formulation

Part A 86.4% Deionized $H_2O$ 0.5% SLES (Cerasynt LP; ISP)

0.1% NaEDTA (Ethylenediaminetetraacetic acid disodium salt dihydrate; Aldrich)

Part B 2.55 Cetyl Stearyl Alcohol (Lanette Wax O; Henkel Corporation)

Part C

10% Aculyn 46 (modified polyethylene glycol, enzymatically modified starch; Rohm & Haas)

Part D 0.5% Conditioning Additive of Example 13

Instructions

Heat Part A to 60° C. with moderately slow stirring. Add Part B to Part A once Part A appears well mixed and homogeneous. Continue slow stirring and allow solution to cool to an ambient temperature. Add Part C while stirring and eventually add Part D.

EXAMPLE 19

Conditioning Shampoo Formulation

Part A

15% Ammonium Lauryl Sulfate (Standapol A, Henkel Corporation)

15% Sodium Lauryl Sulfate (Rhodapon SB-8208/S, Rhône Poulenc)

8% Cocamidopropyl Betaine (Mitratine CB, Rhône Poulenc)

2% Lauramide DEA (Monamid 716, Mona Industries)

Part B

1% Conditioning Additive of Example 13

58.8% Deionized $H_2O$

Part C 0.2% Diazolidinyl Urea/Iodopropynyl Butylcarbamate (Germall Plus, ISP)

Instructions

Heat Part A to 60° C. with moderately slow stirring for approximately ½ hr. or until solution becomes transparent. At the same time, heat Part B to 55° C. while stirring until homogeneous solution is obtained. Add Part B to Part A while continuously stirring. Remove temperature source. Once the resulting solution has reached 45° C., add Part C. Continue to stir (slowly) until the target solution has cooled to an ambient temperature.

In the conditioners and shampoo formulations tested under actual use conditions in comparison with similar formulations with known polymers, the terpolymers of the invention have excellent wet combing, excellent dry feel and softness, and excellent wet feel.

Furthermore they are characterized by excellent styling properties in terms of stiffness, humidity resistance and dry and wet feel.

EXAMPLE 20

Styling Lotion

A styling lotion formulation was prepared in aqueous solution using 1% by weight of the terpolymer of Example 1 and 0.1% preservative.

EXAMPLE 21

Styling Mousse

A concentrate is prepared by dissolving 1 g of the terpolymer of Example 1, 0.1 g of preservative and 98.9 g of deionized water.

A styling mousse formation is prepared by mixing 70 g of the concentrate and 30 of hydrocarbon propellant in an aerosol can provided with a mousse dispenser.

While the invention has been described with particular reference to certain embodiments thereof, it will be understood that changes and modifications may be made which are within the skill of the art. Accordingly, it is intended to be bound only by the following claims, in which:

What is claimed is:

1. A hydrophobically-modified cationic consisting essentially terpolymer of the following monomers;

X, Y and Z;

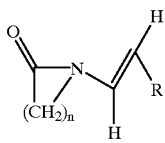
(X)

where:
n is 3 to 6; R is H or $C_1$–$C_5$ alkyl and wt % of X=40–95;

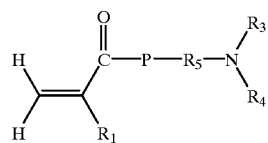
(Y)

where:
P is O or $NR_2$; $R_1$, $R_2$, $R_3$, $R_4$ are independently H or $C_1$–$C_5$ alkyl; $R_5$ is $C_2$–$C_{16}$ alkyl alkylene; and wt % of Y=0.1 to 55; and

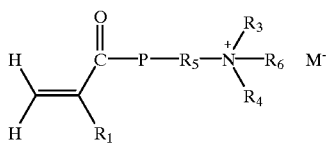
(Z)

where:
P is O or $NR_2$; $R_1$, $R_2$, $R_3$, $R_4$ are independently H or $C_1$–$C_5$ alkyl; $R_5$ is a $C_2$–$C_{16}$ alkylene; $R_6$ is $C_9$–$C_{24}$ alkyl; M is a halide, tosylate or phosphate anion; and wt % of Z=0.25 to 50.

2. A terpolymer according to claim 1 wherein:
X is vinyl pyrrolidone,
Y is dimethylaminopropyl methacrylamide, and
Z is a $C_{12}$–$C_{18}$ alkyl quaternized derivative of an acrylic acid.

3. A terpolymer according to claim 2 wherein X is about 60–90 wt %, Y is about 5–30 wt % and Z is about 1–30 wt %.

4. A terpolymer according to claim 2 wherein Z is $C_{12}$ alkyl quaternized monomer.

5. A terpolymer according to claim 1 wherein the weight average molecular weight is 200,000 to 2,000,000.

6. A terpolymer according to claim 5 wherein said molecular weight is 400,000 to 800,000.

7. A terpolymer according to claim 2 which is water soluble or water dispersible.

8. A terpolymer according to claim 1 which forms a clear humidity resistant, hydrophobic film when cast upon a support surface.

9. A terpolymer according to claim 1 which is surface active and hydrolytically stable.

10. A terpolymer according to claim 1 which is a homogeneous terpolymer.

11. A cosmetic composition including about 0.1 to 10% by weight of the terpolymer of claim 1.

12. A cosmetic composition according to claim 11 which is a hair or skin care product.

\* \* \* \* \*